United States Patent
Silver et al.

(10) Patent No.: US 12,029,843 B2
(45) Date of Patent: *Jul. 9, 2024

(54) MULTI-MODAL FIVE LUMEN GAS CIRCULATION SYSTEM FOR USE IN ENDOSCOPIC SURGICAL PROCEDURES

(71) Applicant: Conmed Corporation, Utica, NY (US)

(72) Inventors: Mikiya Silver, New Haven, CT (US); Michael J. Kane, Clinton, CT (US); Michael J. Augelli, Prospect, CT (US)

(73) Assignee: Conmed Corporation, Largo, FL (US)

( * ) Notice: Subject to any disclaimer, the term of this patent is extended or adjusted under 35 U.S.C. 154(b) by 178 days.

This patent is subject to a terminal disclaimer.

(21) Appl. No.: 17/323,759

(22) Filed: May 18, 2021

(65) Prior Publication Data

US 2021/0268211 A1  Sep. 2, 2021

Related U.S. Application Data

(62) Division of application No. 16/138,354, filed on Sep. 21, 2018, now Pat. No. 11,027,078.

(51) Int. Cl.
*A61M 13/00* (2006.01)
*A61B 1/313* (2006.01)
*A61M 39/10* (2006.01)

(52) U.S. Cl.
CPC ........ *A61M 13/006* (2014.02); *A61M 39/105* (2013.01); *A61B 1/3132* (2013.01);
(Continued)

(58) Field of Classification Search
CPC .............. A61M 13/006; A61M 39/105; A61M 2205/3337; A61M 2205/3344;
(Continued)

(56) References Cited

U.S. PATENT DOCUMENTS 8,795,223 B2  8/2014  Stearns et al.
9,067,030 B2  6/2015  Stearns et al.
(Continued)

FOREIGN PATENT DOCUMENTS

JP  5830625 B2  12/2015
WO  2017/004490 A1  1/2017

OTHER PUBLICATIONS

Extended European Search Report dated May 13, 2022, issued during the prosecution of European Patent Application No. EP 19862818.2.
(Continued)

*Primary Examiner* — Robert J Utama
*Assistant Examiner* — Hamza A Darb
(74) *Attorney, Agent, or Firm* — Locke Lord LLP; Scott D. Wofsy

(57) ABSTRACT

A system is disclosed for performing an endoscopic surgical procedure in a surgical cavity, which includes a multi-modal gas delivery device including a primary gas circulation pump, a secondary gas circulation pump and an insufflation subunit, and an interface plate adapted and configured to engage with the multi-modal gas delivery device and including a connector and a filter seat corresponding to five different lumens, each of which provides a different functionality.

5 Claims, 15 Drawing Sheets

(52) U.S. Cl.
CPC .............. *A61M 2205/3337* (2013.01); *A61M 2205/3344* (2013.01); *A61M 2205/3379* (2013.01); *A61M 2205/3584* (2013.01); *A61M 2205/3592* (2013.01); *A61M 2205/7536* (2013.01); *A61M 2205/7545* (2013.01); *A61M 2210/105* (2013.01); *A61M 2210/1067* (2013.01)

(58) Field of Classification Search
CPC .. A61M 2205/3379; A61M 2205/3584; A61M 2205/3592; A61M 2205/7536; A61M 2205/7545; A61M 2210/105; A61M 2210/1067; A61M 2210/1021; A61M 13/00; A61M 1/85; A61M 1/94; A61B 1/3132; A61B 17/3474; A61B 2218/006
See application file for complete search history.

(56) References Cited

U.S. PATENT DOCUMENTS

| | | | |
|---|---|---|---|
| 9,375,539 | B2 | 6/2016 | Stearns et al. |
| 9,387,295 | B1 | 7/2016 | Mastri et al. |
| 9,387,296 | B1 | 7/2016 | Mastri et al. |
| 9,526,849 | B2 | 12/2016 | Stearns et al. |
| 9,526,886 | B2 | 12/2016 | Mastri et al. |
| 9,907,569 | B2 | 3/2018 | Stearns et al. |
| 2012/0150101 | A1* | 6/2012 | Stearns ................ A61M 13/00 604/24 |
| 2015/0112246 | A1 | 4/2015 | Palmerton et al. |
| 2016/0106934 | A1* | 4/2016 | Hiraga ................ A61B 1/3132 604/26 |
| 2016/0106952 | A1 | 4/2016 | Mastri et al. |
| 2016/0287817 | A1 | 10/2016 | Mastri et al. |
| 2016/0317764 | A1 | 11/2016 | Koth et al. |
| 2017/0361084 | A1 | 12/2017 | Zergiebel et al. |
| 2018/0221597 | A1 | 8/2018 | Silver |
| 2018/0221599 | A1 | 8/2018 | Hiraga et al. |
| 2018/0256204 | A1 | 9/2018 | Silver et al. |

OTHER PUBLICATIONS

International Search Report issued in corresponding PCT Patent Application No. PCT/US2019/051914, dated Jan. 10, 2020.
Extended European Search Report dated Apr. 4, 2023, issued during the prosecution of European Patent Application No. EP 22216171.3.

\* cited by examiner

MULTI-MODAL FIVE LUMEN GAS CIRCULATION SYSTEM FOR USE IN ENDOSCOPIC SURGICAL PROCEDURES

This Application is a Divisional of U.S. patent application Ser. No. 16/138,354 filed Sep. 21, 2018, now U.S. Pat. No. 11,027,078 issued Jun. 8, 2021, the entire contents of which is incorporated herein by reference in its entirety.

BACKGROUND OF THE INVENTION

1. Field of the Invention

The subject invention is directed to endoscopic surgery, and more particularly, to a surgical gas circulation system that is adapted and configured for multi-modal operation including insufflation, recirculation and smoke evacuation using a filtered tube set having five separate lumens.

2. Description of Related Art

Endoscopic surgical techniques are well known. Indeed, laparoscopic surgical procedures performed in the abdominal cavity, such as cholecystectomies, appendectomies, hernia repair and nephrectomies have become commonplace. Benefits of such minimally invasive procedures include reduced trauma to the patient, reduced opportunity for infection, and decreased recovery time. Such procedures are typically performed through a device known as a trocar or cannula, which facilitates the introduction of laparoscopic instruments into the abdominal cavity of a patient.

Endoscopic surgical procedures performed in other surgical cavities or areas of the body include thoracoscopic surgical procedures performed in the thoracic cavity of a patient, as well as, endo-luminal surgical procedures, such as trans-anal and trans-esophageal surgical procedures.

Endoscopic surgical procedures commonly involve filling or "insufflating" the surgical cavity with a pressurized fluid, such as carbon dioxide, to create an operating space. In the case of laparoscopy in the abdominal cavity, this is referred to as a pneumoperitoneum. Insufflation can be carried out by a surgical access device, such as a trocar, equipped to deliver insufflation fluid, or by a separate insufflation device, such as an insufflation (veress) needle.

The trocar must also provide a way to maintain the pressure within the surgical cavity by sealing between the trocar and the surgical instrument being used, while still allowing at least a minimum amount of freedom of movement for the surgical instruments. Mechanical seals are typically provided on trocars to prevent the escape of insufflation gas from the surgical cavity. These seals often comprise a duckbill-type valve made of a relatively pliable material, which seals around an outer surface of a surgical instrument passing through the trocar.

SurgiQuest, Inc., a wholly owned subsidiary of ConMed Corporation has developed unique gas sealed surgical access devices that permit ready access to an insufflated surgical cavity without the need for conventional mechanical seals, as described, for example, in U.S. Pat. Nos. 8,795,223 and 9,907,569, the disclosures of which are herein incorporated by reference in their entireties. These gas sealed devices have an inner tubular body portion that defines a central lumen for introducing surgical instruments to the surgical cavity and an outer tubular body portion that defines an annular outer lumen surrounding the inner tubular body portion for delivering insufflation gas to the surgical cavity and for facilitating periodic sensing of cavity pressure.

During use, pressurized gas is delivered to the access device, where it is accelerated by internal jet nozzles to create a gaseous sealing zone within the central lumen of the access device. Gas that has been used to generate the gaseous sealing zone is carried away from the access device by way of a suction line.

These dual-lumen gas sealed access devices are designed for use with a unique multi-modal surgical gas delivery device, as described in commonly assigned U.S. Pat. Nos. 9,067,030 and 9,526,849, the disclosures of which are herein incorporated by reference. This gas delivery device includes an insufflation subunit for delivering insufflation gas to the outer annular lumen of the access device, and for taking period pressure readings from the surgical cavity. The gas delivery device further incudes a gas circulation pump for delivering pressurized gas to the nozzle jets located within in the access device and for carrying away spent gas from the access device, thereby forming a gas recirculation path between the pump and the access port.

Those skilled in the art will readily appreciate that electrocautery devices are regularly used during endoscopic surgical procedures. These devices are used to cut and/or coagulate tissue, and typically give off smoke during this process. The smoke can cloud the vision of the endoscopic camera, leading to delays in surgery or requiring the surgical team to evacuate that smoke from the surgical cavity.

It is known to utilize a dual-lumen gas sealed access device in conjunction with a multi-modal gas delivery device to remove smoke filled gas from a surgical cavity, while maintaining a gaseous seal within the access device. In this mode of operation, smoke removal is conducted by way of the gas recirculation path used to generate the gaseous seal in the access device, which is filtered on both the input and output legs of the path. Moreover, smoke filled gas will flow up through the central lumen of the access device and into the gas recirculation path by way of a "chimney" effect, where it will be filtered within the suction line.

While this method of smoke evacuation has been somewhat effective, it has certain shortcomings. First, the smoke evacuation mode of the current multi-modal gas delivery device described in U.S. Pat. Nos. 9,067,030 and 9,526,849 does not operate continuously. Rather, it toggles on and off, because the addition of insufflation gas through the outer annular lumen of the access device must be interrupted so that the insufflation subunit within the gas delivery device can accurately sense cavity pressure. Second, some of the smoke filled gas flows up through the central lumen of the gas sealed access device can find its way out of the open end of the access device, where it is released into the operating room, creating undesirable odors.

It would be beneficial therefore to separate the smoke evacuation function from the gas recirculation function of the gas sealed access port so that smoke evacuation can be performed continuously and so that smoke filled gas is not unnecessarily released into the operating room environment through the open end of the gas sealed access port.

The subject invention provides a beneficial solution to these problems by incorporating a second gas circulation pump into the multi-modal gas delivery device, which is dedicated to smoke evacuation, thereby separating smoke evacuation from the gas recirculation path used to create the gaseous sealing zone in a gas sealed access device.

SUMMARY OF THE DISCLOSURE

The subject invention is directed to a new and useful system for performing an endoscopic surgical procedure in a surgical cavity, which includes a multi-modal gas delivery device including a primary gas circulation pump, a secondary gas circulation pump and an insufflation subunit, and an interface plate adapted and configured to engage with the multi-modal gas delivery device and including a connector and a filter seat corresponding to each of five separate and distinct lumens.

The first lumen is an insufflation and sensing lumen for delivering insufflation gas from the insufflation subunit to the surgical cavity and for facilitating sensing of surgical cavity pressure. The second lumen is a gas delivery lumen for delivering pressurized gas from the primary gas circulation pump to a gas sealed access device. The third lumen is a gas return lumen for returning gas used to generate a gaseous seal within the gas sealed access device back to the primary gas circulation pump. The fourth lumen is a smoke evacuation lumen for removing smoke filled gas from the surgical cavity by way of the secondary gas circulation pump. The fifth lumen is a recirculation supply lumen for returning filtered gas back to the surgical cavity from the secondary gas circulation pump.

In one embodiment of the subject invention, the insufflation and sensing lumen is attached to a respective connector of the interface plate, and a modular bi-directional filter canister is seated on the interface plate to communicate with the attached lumen. Furthermore, a distal end of the insufflation and sensing lumen has a coupling that is adapted and configured to connect with a valve sealed access device.

In another embodiment of the subject invention, the insufflation and sensing lumen, the gas delivery lumen and the gas return lumen are attached to respective connectors of the interface plate, and modular bi-directional filter canisters are seated on the interface plate to communicate with each of the attached lumens. Furthermore, distal ends of the insufflation and sensing lumen, the gas delivery lumen and the gas return lumen are attached to a tri-lumen coupling that is adapted and configured to connect with the gas sealed access device. Alternatively, distal ends of the gas delivery lumen and the gas return lumen are attached to a bi-lumen coupling that is adapted and configured to connect with the gas sealed access device, and a distal end of the insufflation and sensing lumen has a coupling that is adapted and configured to connect with a valve sealed access device.

In yet another embodiment of the subject invention, the smoke evacuation lumen and the recirculation supply lumen are attached to respective connectors of the interface plate, and filter canisters are seated on the interface plate to communicate with each of the attached lumens. Furthermore, a distal end of the smoke evacuation lumen has a coupling that is adapted and configured to connect with a first valve sealed access device and a distal end of the recirculation supply lumen has a coupling that is adapted and configured to connect with a second valve sealed access device.

In still another embodiment of the subject invention, the insufflation and sensing lumen, the smoke evacuation lumen and the recirculation supply lumen are attached to respective connectors of the interface plate, and filter canisters are seated on the interface plate to communicate with each of the attached lumens. Furthermore, a distal end of the insufflation and sensing lumen has a coupling that is adapted and configured to connect with a first valve sealed access device, a distal end of the smoke evacuation lumen has a coupling that is adapted and configured to connect with a second valve sealed access device and a distal end of the recirculation supply lumen has a coupling that is adapted and configured to connect with a third valve sealed access device.

In an ultimate embodiment of the subject invention, the insufflation and sensing lumen, the gas delivery lumen, the gas return lumen, the smoke evacuation lumen and the recirculation supply lumen are all attached to respective connectors of the interface plate, and modular filter canisters are seated on the interface plate to communicate with each of the attached lumens. Furthermore, distal ends of the insufflation and sensing lumen, the gas delivery lumen and the gas return lumen are attached to a tri-lumen coupling that is adapted and configured to connect with the gas sealed access device, a distal end of the smoke evacuation lumen has a coupling that is adapted and configured to connect with a first valve sealed access device and a distal end of the recirculation supply lumen has a coupling that is adapted and configured to connect with a second valve sealed access device.

Alternatively, distal ends of the gas delivery lumen and the gas return lumen are attached to a bi-lumen coupling that is adapted and configured to connect with the gas sealed access device, a distal end of the insufflation and sensing lumen has a coupling that is adapted and configured to connect with a first valve sealed access device, a distal end of the smoke evacuation lumen has a coupling that is adapted and configured to connect with a second valve sealed access device and a distal end of the recirculation supply lumen has a coupling that is adapted and configured to connect with a third valve sealed access device.

It is envisioned that each filter seat of the interface plate would be configured to receive a uniform or common modular filter canister that includes a pleated filter element for filtering gas flowing therethrough. Those skilled in the art will readily appreciate that the modularity and commonality of the filter canisters provides benefits and advantages in terms of decreased manufacturing costs, reduced inventory and ease of assembly. Each modular filter canister is preferably attached to a respective filter seat by conventional means known in the art such as, for example, an adhesive, ultrasonic welding, spin welding, and laser welding or by way of a threaded fit or an interference fit.

Preferably, the filter element in each canister is configured for bi-directional flow so that it can be utilized to filter a flow of clean pressurized gas coming from the outlet side of a gas circulation pump or an outlet flow of spent or smoke filled gas going to the suction side of a gas circulation pump. The bi-directional filter element within each canister is preferably selected from a group of filter media consisting of a pleated filter media, a woven polymer mesh filter media, a non-woven polymer mesh filter media, sintered metal filter media, a sintered polymer filter media, an activated carbon filter media, and a particulate filter media. Each filter canister also includes means for detected a fluid level within the filter canister. This can include an optical sensors or the like.

It is envisioned that the interface plate could include a permanent or integral filter canister operatively associated with the filter seat that communicates with the insufflation and sensing lumen, while the four other filter seats would each have the previously described modular filter canister associated therewith. This is because nearly every embodiment or version of the interface plate would likely include the insufflation and sensing lumen. It is the most often gas path used in the embodiment of the subject invention described herein.

It is also envisioned that the interface plate would include means for communicating information to a controller in the gas delivery device identifying which of the five lumens is attached to the interface plate. The information received from an interface plate of a tube set is preferably communicated to the gas delivery device by way of an RFID communication link, an NFC communication link, a Bluetooth communication link, a WiFi communication link or by way of microswitches.

The subject invention is also directed to an interface plate for a multi-modal gas delivery device used in performing an endoscopic surgical procedure in a surgical cavity. The interface plate includes a first connector for an insufflation and sensing lumen that delivers insufflation gas from an insufflation subunit in the gas delivery device to the surgical cavity and facilitates sensing of surgical cavity pressure, a second connector for a gas delivery lumen that delivers pressurized gas from a primary gas circulation pump in the gas delivery device to a gas sealed access device, a third connector for a gas return lumen that returns gas used to generate a gaseous seal within the gas sealed access device back to the primary gas circulation pump, a fourth connector for a smoke evacuation lumen that removes smoke filled gas from the surgical cavity by way of a secondary gas circulation pump in the gas delivery device, and a fifth connector for a recirculation supply lumen that returns filtered gas back to the surgical cavity from the secondary gas circulation pump.

The interface plate further includes a filter seat corresponding to each of the five connectors for receiving a respective filter canister. In one embodiment of the subject invention, an insufflation and sensing lumen is attached to the first connector of the interface plate, and a filter canister is seated on the interface plate to communicate with the attached lumen. In another embodiment of the subject invention, an insufflation and sensing lumen is attached to the first connector of the interface plate, a gas delivery lumen is attached to the second connector of the interface plate and a gas return lumen is attached to the third of the interface plate, and filter canisters are seated on the interface plate to communicate with each of the attached lumens.

In yet another embodiment of the subject invention, a smoke evacuation lumen is attached to the fourth connector of the interface plate and a recirculation supply lumen is attached to the fifth connector of the interface plate, and filter canisters are seated on the interface plate to communicate with each of the attached lumens. In still another embodiment of the subject invention, an insufflation and sensing lumen is attached to the first connector of the interface plate, a smoke evacuation lumen is attached to the fourth connector of the interface plate and a recirculation supply lumen is attached to the fifth connector of the interface plate, and filter canisters are seated on the interface plate to communicate with each of the attached lumens.

In an ultimate embodiment of the interface plate of the subject invention, an insufflation and sensing lumen is attached to the first connector of the interface plate, a gas delivery lumen is attached to the second connector of the interface plate, a gas return lumen is attached to the third connector of the interface plate, a smoke evacuation lumen is attached to the fourth connector of the interface plate and a recirculation supply lumen is attached to the fifth connector of the interface plate, and filter canisters are seated on the interface plate to communicate with each of the attached lumens.

The subject invention is also directed to a multi-modal gas delivery device for performing an endoscopic surgical procedure in a surgical cavity, which includes an insufflation subunit for delivering insufflation gas from a gas source to the surgical cavity and for sensing pressure within the surgical cavity, a primary gas circulation pump for delivering pressurized gas to a gas sealed access port so as to generate a gaseous seal therein and thereby maintain a stable pressure within the surgical cavity and for receiving gas returning from the gas sealed access port that was used to form the gaseous seal, and a secondary gas circulation pump for continuously evacuating smoke filled gas from the surgical cavity. The secondary pump can operate regardless of the sensed pressure within the surgical cavity. Preferably, the secondary gas circulation pump is further configured to return filtered gas to the surgical cavity.

The gas delivery device further comprises a controller for initiating an operating mode from a group of operating modes including: i) an insufflation mode driven by the insufflation subunit; ii) an insufflation and gas circulation mode driven by the insufflation subunit and the primary gas circulation pump; iii) a smoke evacuation and gas return mode driven by the secondary gas circulation pump; iv) an insufflation and smoke evacuation mode driven by the insufflation subunit and the secondary gas circulation pump; v) an insufflation, smoke evacuation and gas return mode driven by the insufflation subunit and the secondary gas circulation pump; and vi) an insufflation and gas circulation mode driven by the insufflation subunit and the primary gas circulation pump, together with smoke evacuation and gas return driven by the secondary gas circulation pump.

Preferably, the controller is adapted and configured to determine which operating mode to initiate based upon information received from an interface plate of a tube set operatively associated therewith. The information received from an interface plate of a tube set is preferably communicated to the gas delivery device by way of an RFID communication link, an NFC communication link, a Bluetooth communication link, a WiFi communication link or by way of micro-switches.

These and other features of the gas circulation system of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the gas circulation system of the subject invention without undue experimentation, preferred embodiments thereof will be described in detail herein below with reference to the FIGS. wherein.

DETAILED DESCRIPTION OF THE PREFERRED EMBODIMENTS

Figure 1:
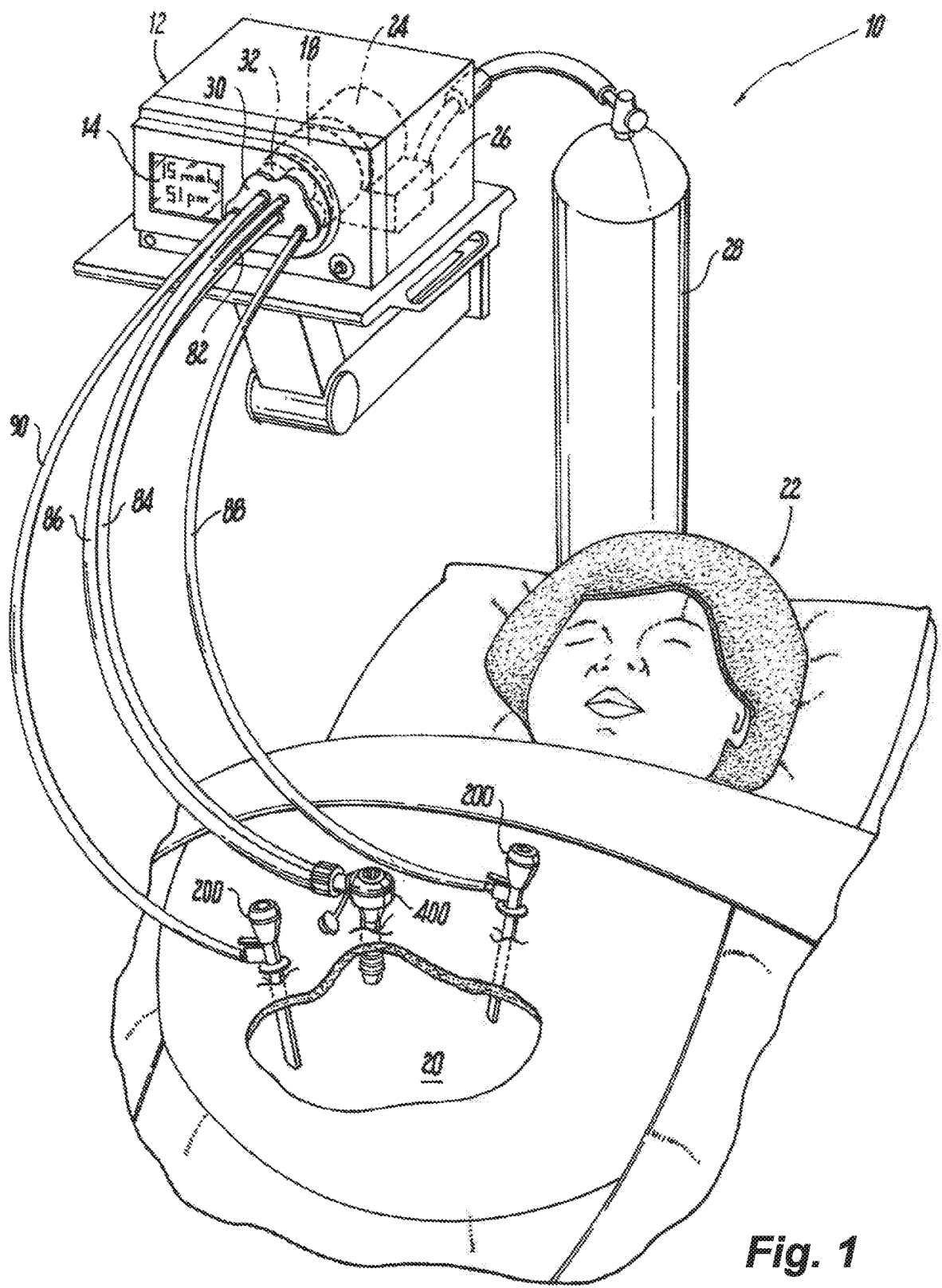
FIG. 1 is a perspective view of the gas circulation system of the subject invention in use during the performance of a laparoscopic surgical procedure, which includes a multi-modal gas delivery device having an interface plate connected to a tri-lumen tube set associated with a gas sealed access port, along with a smoke evacuation lumen and a recirculation supply lumen associated with two valve sealed access ports.

Referring now to the drawings wherein like reference numerals identify similar structural elements and features of the subject invention, there is illustrated in FIG. 1 a gas circulation system for performing an endoscopic surgical procedure in a surgical cavity of a patient, and more particularly, for performing a laparoscopic surgical procedure in the abdominal cavity of a patient that is constructed in accordance with a preferred embodiment of the subject disclosure and is designated generally by reference numeral 10.

Those skilled in the art will readily appreciate that the gas circulation system 10 of the subject invention can be used for performing other types of endoscopic procedures, aside from laparoscopic procedures. For example, this system 10 can be used in the performance of thoracoscopic surgical procedures in the thoracic cavity of a patient, as well as, the performance of endo-luminal surgical procedures, such as trans-anal and trans-esophageal surgical procedures.

Referring to FIG. 1, the gas circulation system 10 of the subject invention is specifically designed to cooperate with a programmable multi-modal gas delivery device 12. The gas delivery device 12 is based upon the multi-modal gas delivery device described, for example, in commonly assigned U.S. Pat. No. 9,375,539, the disclosure of which is herein incorporated by reference in its entirety.

The gas delivery device 12 includes a graphical user interface 14 for setting operating parameters, and more particularly, for interacting with an internal controller 16 (see FIG. 2) that is programmable to operate the gas delivery device 12 in a variety of different operating modes, depending upon the demands of a particular endoscopic surgical procedure.

Figure 1A:
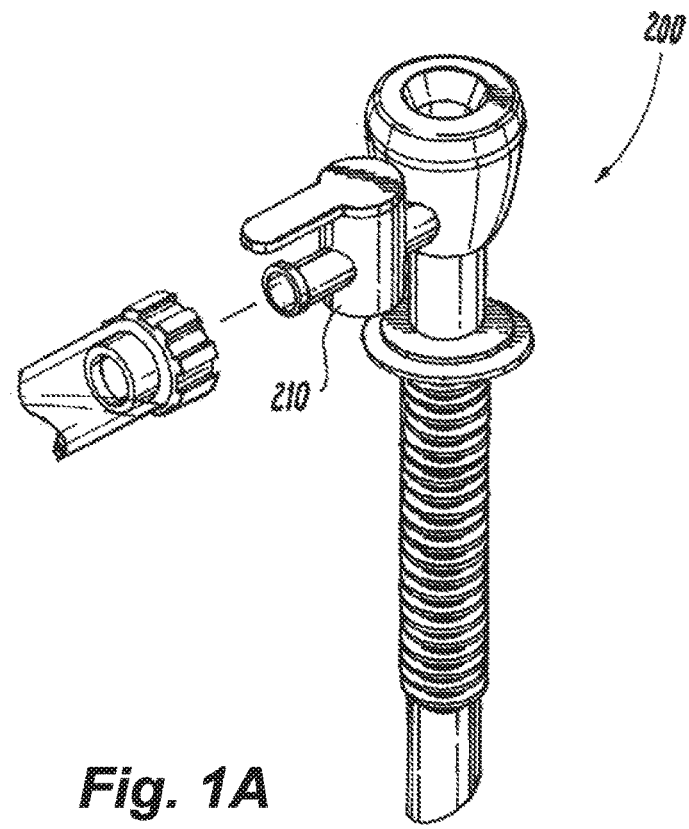
FIG. 1A is a perspective view of a valve sealed access port with a conventional luer fitting for coupling with a single lumen connector.

More particularly, as explained in greater detail below, and with reference to FIGS. 1A through 1C, the controller 16 of the gas delivery device 12 of the subject invention is programmed or otherwise configured to perform: i) insufflation through a single valve sealed access port 200 which has a conventional luer connector 210 (see FIG. 1A); ii) insufflation through a valve sealed access port 200 and gas circulation through a single-lumen gas sealed access port 300 which has a bi-lumen connector 310 (see FIG. 1B); iii) insufflation and gas circulation through a dual lumen gas sealed access port 400 which has a tri-lumen connector 410 (see FIG. 1C); iv) evacuation of smoky gas and filtered gas return through two separate valve sealed access ports 200; v) insufflation and evacuation of smoky gas through two separate valve sealed access ports 200; vi) insufflation, evacuation of smoky gas and filtered gas return through three separate valve sealed access ports 200; and vii) insufflation and gas circulation through a dual lumen gas sealed access port 300, together with evacuation of smoke filled gas and filtered gas return through two separate valve sealed access ports 200.

Figure 2:
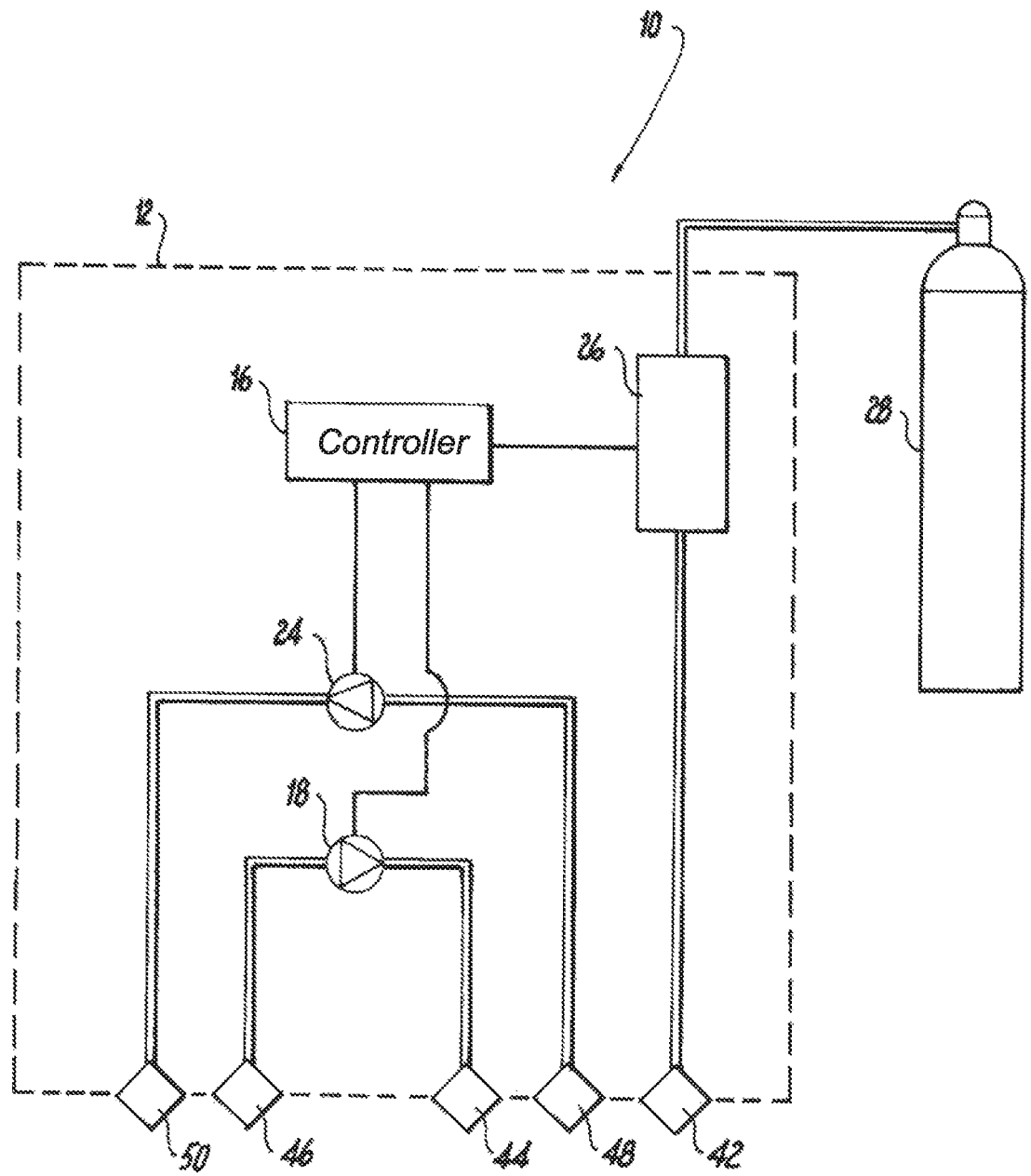
FIG. 2 is a schematic representation of the multi-modal gas delivery device shown in FIG. 1, which includes an insufflation subunit and a primary gas circulation pump for communicating with the insufflation and sensing lumen, the gas delivery lumen and the gas return lumen, and a secondary gas circulation pump for communicating with the smoke evacuation lumen and the recirculation supply lumen.

Referring once again to FIG. 1 in conjunction with the schematic diagram shown in FIG. 2, the gas delivery device 12 of the subject invention further includes a primary gas circulation pump 18 for facilitating the circulation/recirculation of pressurized gas relative to the surgical cavity 20 of a patient 22, a secondary gas circulation pump 24 for facilitating smoke evacuation from the surgical cavity 20 of the patient 22, and an insufflation subunit 26 for delivering insufflation gas from a gas source 28 to the surgical cavity 20 of the patient 22, as well as sensing pressure within the surgical cavity 18 of patient 22 periodically.

The gas delivery system 10 of the subject invention further includes an interface plate 30 that is adapted and configured to engage with the multi-modal gas delivery device 12 and it is designed for connection with as many as five different lumens or tubes, each of which has a different functionality, depending upon a selectively or automatically activated mode of operation, as explained in more detail below. More particularly, the front face of the gas delivery device 12 has a complementary reception cavity 32 for receiving and engaging with the interface plate 30.

Figure 3:
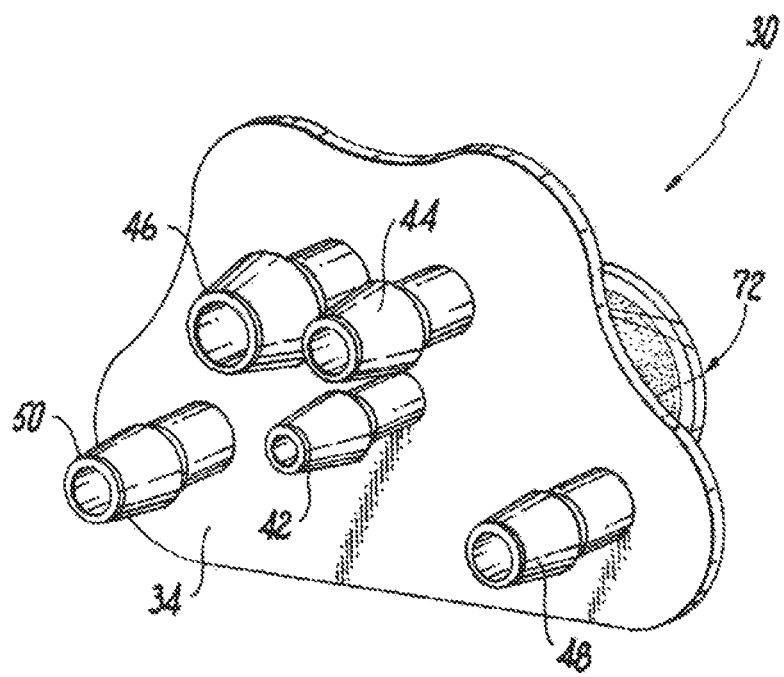
FIG. 3 is a perspective view of the interface plate of the subject invention, as viewed from the front or external surface thereof, illustrating the five connectors provided thereon.
Figure 4:
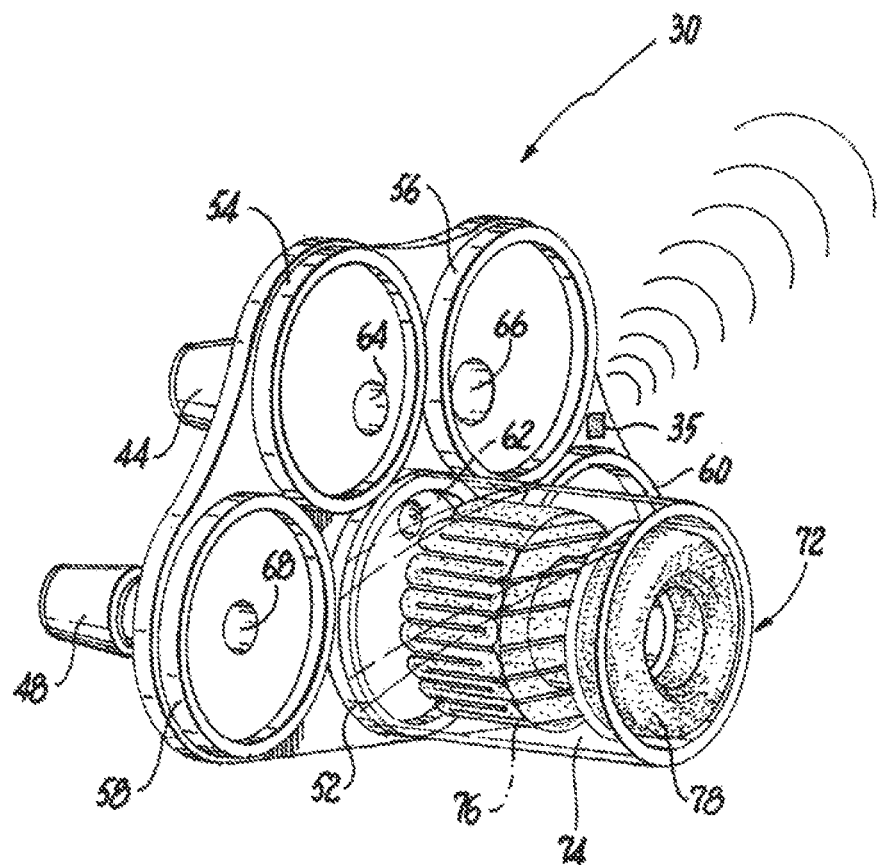
FIG. 4 is a perspective view of the interface plate of the subject invention, as viewed from the rear or internal surface thereof, illustrating the five filter seats thereof, one of which has a modular filter unit seated therein.

Referring now to FIGS. 3 and 4, the interface plate 30 of the subject invention includes a front or exterior surface 34 and a rear or internal surface 36. As shown in FIG. 3, the front surface 34 of interface plate 30 includes a first connector 42 for connecting with an insufflation and sensing lumen for delivering insufflation gas from the insufflation subunit 26 to the surgical cavity 20 and for facilitating sensing of surgical cavity pressure by way of a valve sealed access device 200. It is envisioned and well within the scope of the subject disclosure that that sealed access device 200 could be replaced by another device including for example, a veress needle or another type of surgical access device or trocar adapted to deliver insufflation gas to a surgical cavity, including any of the access device disclosed herein.

The front surface 34 of interface plate 30 also includes a second connector 44 for connecting with a gas delivery lumen for delivering pressurized gas from the primary gas circulation pump 18 to a gas sealed access device 300 or 400. The front surface 34 of interface plate 30 further includes a third connector 46 for connecting with a gas return lumen for returning gas used to generate a gaseous seal within the gas sealed access device 300 or 400 back to the primary gas circulation pump 18.

The front surface 34 of the interface plate 30 also includes a fourth connector 48 for connecting with a smoke evacuation lumen that removes smoke filled gas from the surgical cavity 20 by way of the secondary gas circulation pump 24 by way of a valve sealed access port 200. The front surface 34 of interface plate 30 further includes a fifth connector 50 for connection with a recirculation supply lumen for returning filtered gas back to the surgical cavity 20 from the secondary gas circulation pump 24 by way of a valve sealed access port 200.

As best seen in FIG. 4, the rear surface 36 of interface plate 30 includes a first circular filter seat 52 with a port 62 for communicating with the first connector 42, a second circular filter seat 54 with a port 64 communicating with the second connector 44, a third circular filter seat 56 with a port 66 communicating with the third connector 46, a fourth circular filter seat 58 with a port 68 communicating with the fourth connector 48, and a fifth circular filter seat 60 with a port 70 communicating with the fifth connector 50.

As illustrated in FIG. 4, a modular filter unit 72 that includes a cylindrical canister 74 is seated within the first filter seat 52. As explained in more detail below, identical filter units can be readily seated in each of the five seating areas in the rear surface 36 of interface plate 30, depending upon the activated mode of operation. Those skilled in the art will readily appreciate that the modularity and commonality of these filter units provides benefits and advantages in terms of decreased manufacturing costs, reduced inventory and ease of assembly. Each modular filter unit 72 is preferably attached to a respective filter seat by conventional means known in the art such as, for example, an adhesive, ultrasonic welding, spin welding, and laser welding or by way of a threaded fit or an interference fit to enable ready replacement of a used filter module.

The modular canister 74 of filter unit 72 contains a filter element 76 for filtering gas flowing therethrough, and an elastomeric face seal 78 for sealing against a complementary sealing surface located within the reception cavity 32 of gas delivery device 12 (not shown).

While the filter element 76 of filter unit 72 is shown as a pleated filter element, it is envisioned that the filter element 76 can be selected from a group of different types of filter media including, for example, pleated filter media, woven polymer mesh filter media, non-woven polymer mesh filter media, sintered metal filter media, sintered polymer filter media, activated carbon filter media, particulate filter media and the like. Regardless of the material that is used within the filter unit, it will be a material that is configured to facilitate two-way, bi-directional gas flow. That is, the filter element 76 in each canister 74 is configured so that it can be readily utilized to filter a flow of clean pressurized gas coming from the outlet side of one of the gas circulation pumps 18, 24 or a flow of spent or smoke filled gas going to the suction side of one of the gas circulation pumps 18, 24.

Figure 5:
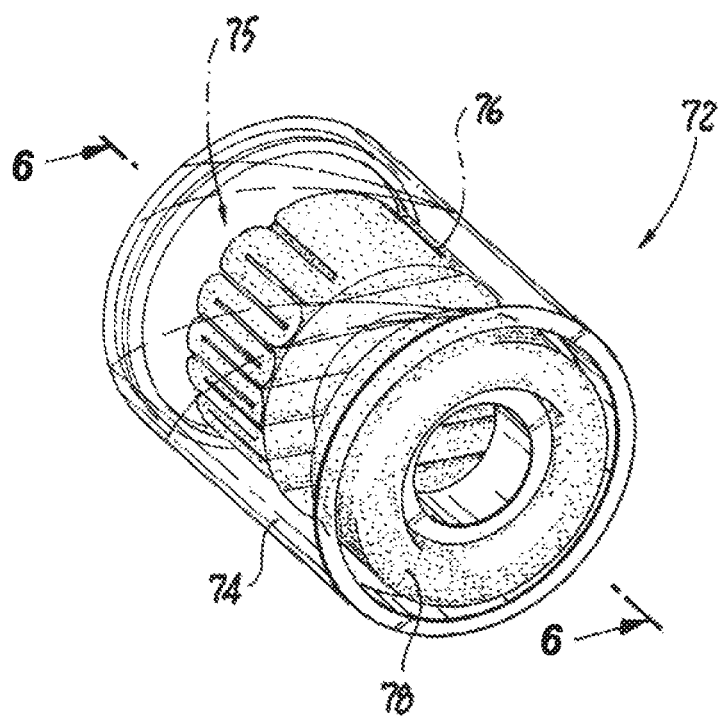
FIG. 5 is an enlarged perspective view of a modular filter unit constructed in accordance with a preferred embodiment of the subject invention, which includes an external face seal and an internal pleated filter element.
Figure 6:
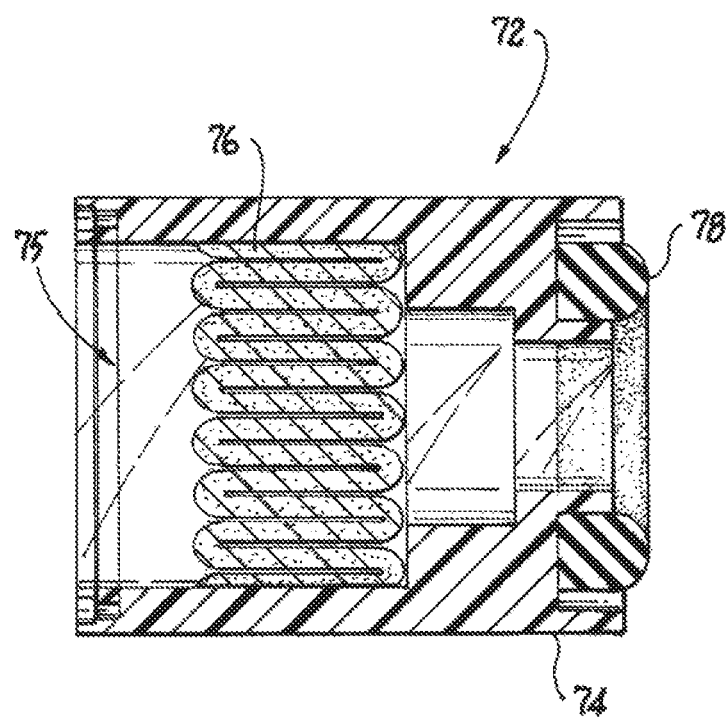
FIG. 6 is cross-sectional view of the filter compartment of the subject invention, taken along line 6-6 of FIG. 5.

As best seen in FIGS. 5 and 6, the filter canister 74 of filter unit 72 also includes an internal reservoir 75 for accumulating any fluids that are drawn into the canister 74 under suction or otherwise during a surgical procedure. The reservoir 75 preferably includes a mechanism (not shown) for detecting a fluid level within the filter canister 74, such as for example, an optical sensing mechanism as described in commonly assigned U.S. Pat. No. 9,067,030, the disclosure of which is incorporated herein by reference.

Figure 7:
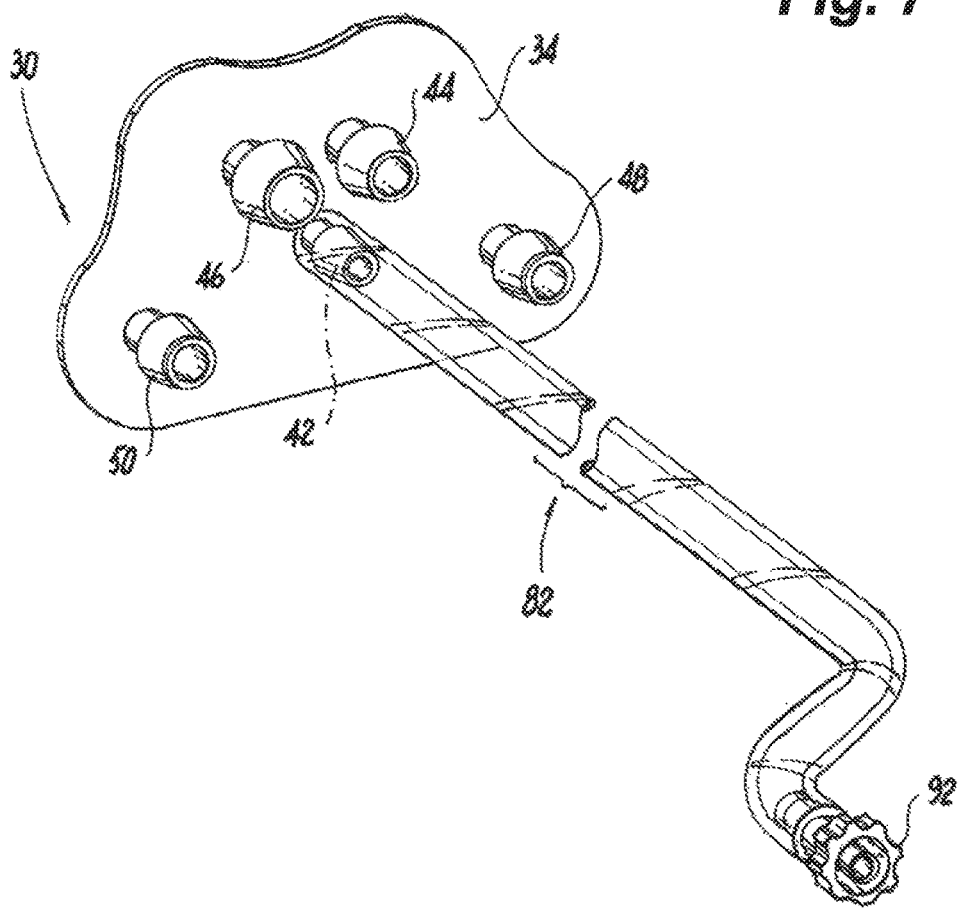
FIGS. 7 and 8 are perspective views of the interface plate of the subject invention, wherein an insufflation and sensing lumen is attached thereto, along with a single filter unit.
Figure 8:
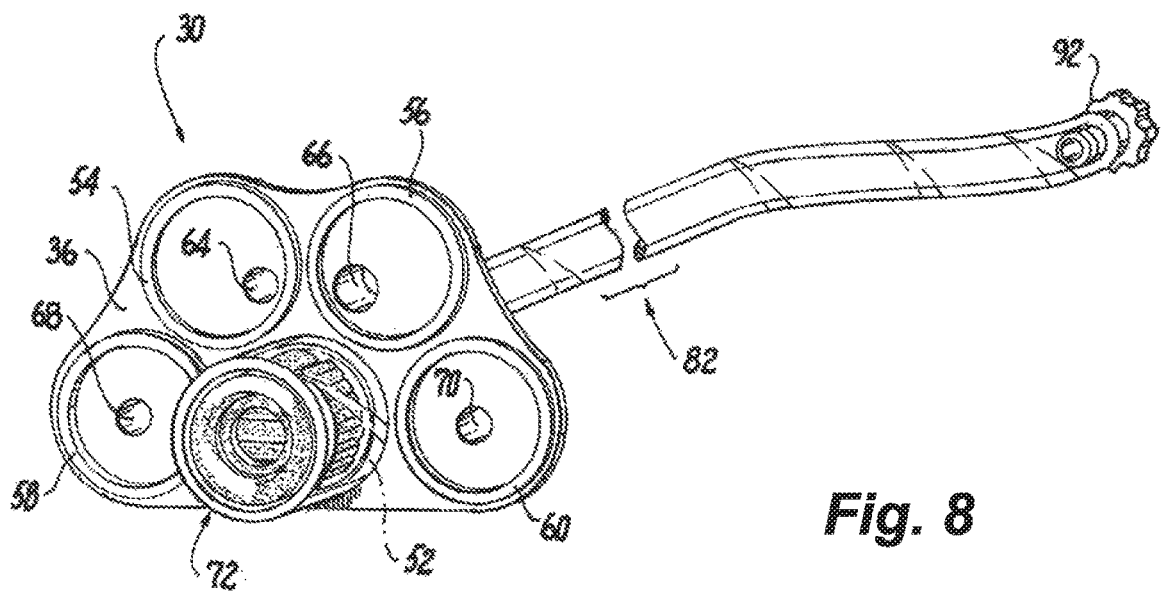

Referring now to FIGS. 7 and 8, which also relates to FIGS. 3 and 4, there is illustrated an interface plate 30 of the subject invention that is adapted and configured for use with the gas delivery device 12 in an insufflation only operating mode. In this instance, an insufflation and sensing lumen 82 is attached to the first connector 42 of the interface plate 30. The distal end of the insufflation and sensing lumen 82 has a convention luer type coupling 92 that is adapted and configured to connect with the connector 210 of a valve sealed access device 200 (see FIG. 1A).

Figure 9:
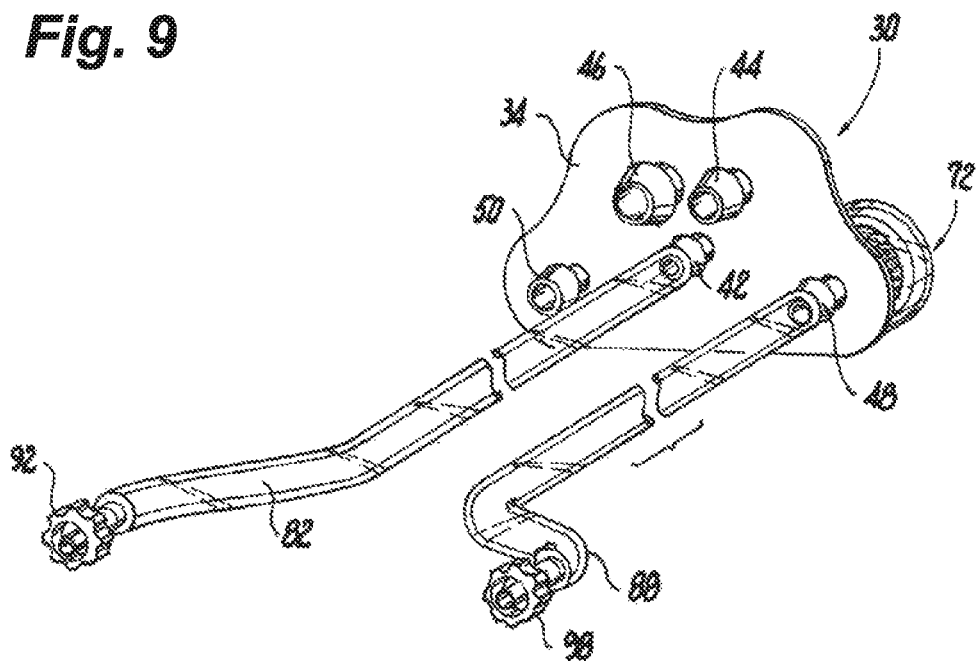
FIGS. 9 and 10 are perspective views of the interface plate of the subject invention, wherein an insufflation and sensing lumen is attached thereto, together with a smoke evacuation lumen, along with two associated filter units.
Figure 10:
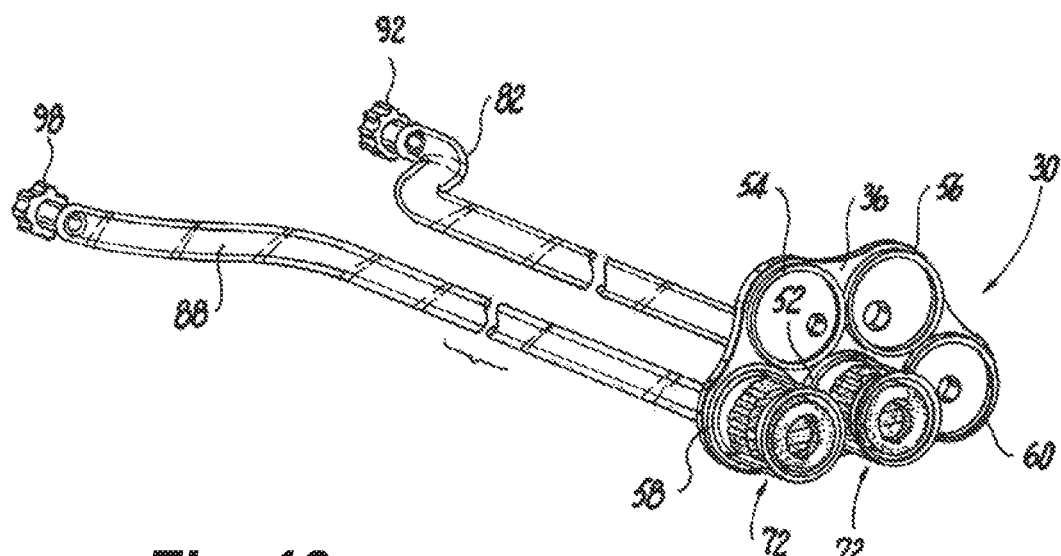

Referring now to FIGS. 9 and 10, there is illustrated an interface plate 30 of the subject invention that is adapted and configured for use with the gas delivery device 12 in an operating mode involving insufflation/sensing and evacuation of smoky gas through two separate valve sealed access ports 200. In this instance, the insufflation and sensing lumen 82 is attached to the first connector 42 of the interface plate 30, and a smoke evacuation lumen 88 is attached to the fourth connector 48 of the interface plate 30. The distal end of the insufflation and sensing lumen 82 has a coupling 92 that is adapted and configured to connect with the connector 210 of a first valve sealed access device 200 and the distal end of the smoke evacuation lumen 88 has a coupling 98 that is adapted and configured to connect with the connector 210 of a second valve sealed access device 200. As best seen in FIG. 10, in this embodiment, there are two filter units 72 associated with the rear surface 36 of interface plate 30, wherein one is associated with filter seat 52 and the other is associated with filter seat 58.

Figure 11:
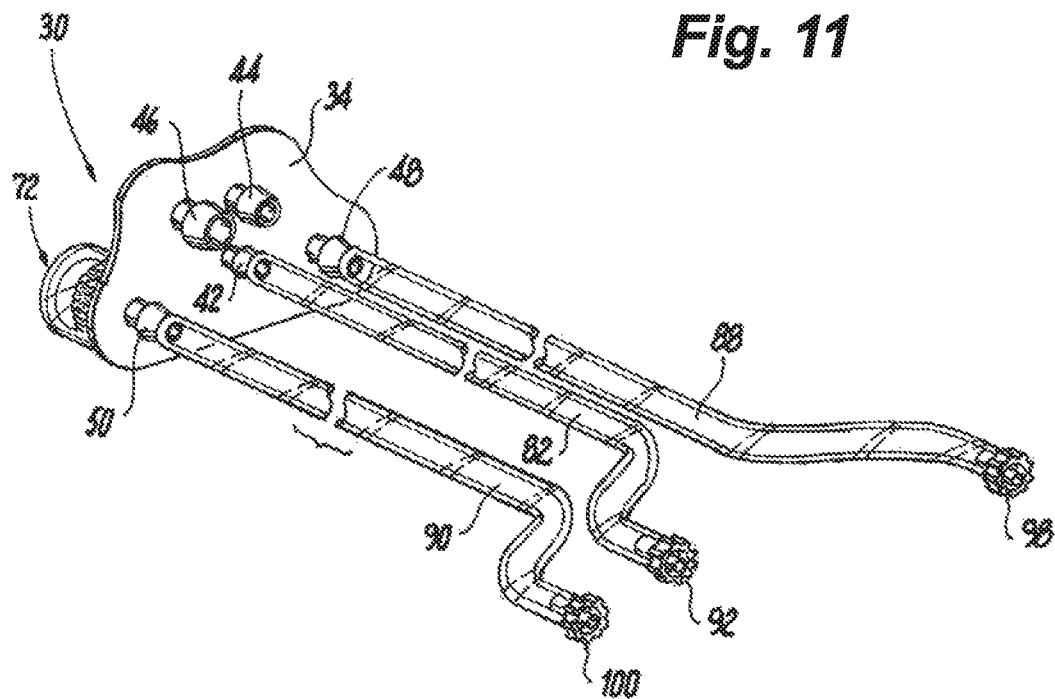
FIGS. 11 and 12 are perspective views of the interface plate of the subject invention, wherein an insufflation and sensing lumen is attached thereto, together with a smoke evacuation lumen and a recirculation supply lumen, along with three associated filter units.
Figure 12:
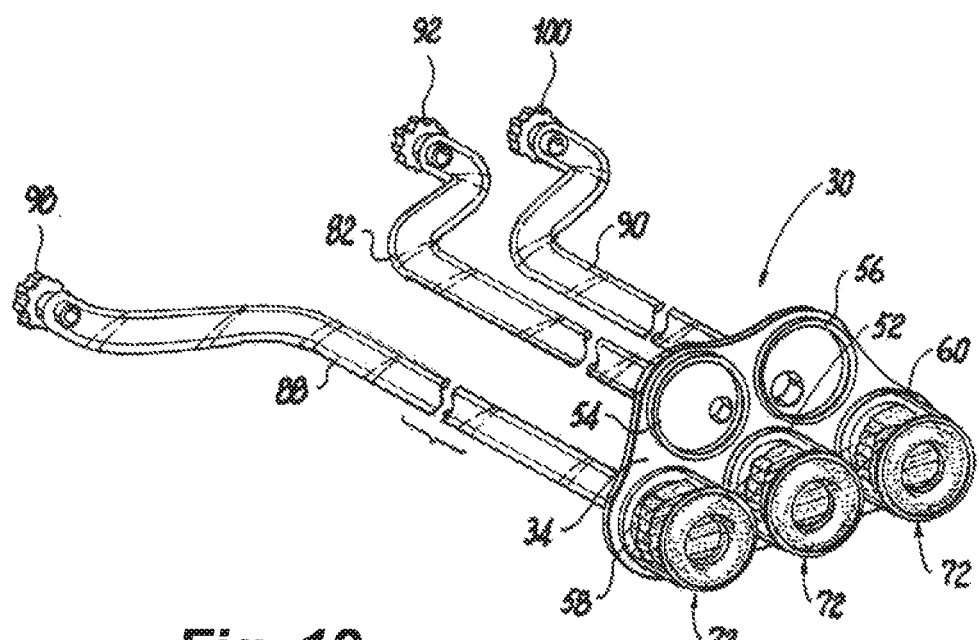

Referring to FIGS. 11 and 12, there is illustrated another embodiment of the interface plate 30 of the subject invention, which is adapted and configured for use with the gas delivery device 12 in an operating mode that involves insufflation, smoke evacuation and the return of filtered gas through three separate valve sealed access ports 200. In this instance, the insufflation and sensing lumen 82 is attached to the first connector 42 of the interface plate 30, the smoke evacuation lumen 88 is attached to the fourth connector 48 of the interface plate 30, and a recirculation supply lumen 90 is attached to the fifth connector 50 of the interface plate 30.

The distal end of the insufflation and sensing lumen 82 has a coupling 92 that is adapted and configured to connect with the connector 210 of a first valve sealed access device 200, the distal end of the smoke evacuation lumen 88 has a coupling 98 that is adapted and configured to connect with the connector 210 of a second valve sealed access device 200, and the distal end of the recirculation supply lumen 90 has a coupling 100 that is adapted and configured to connect with the connector 210 of a third valve sealed access device 200. As best seen in FIG. 12, in this embodiment, there are separate three filter units 72 associated with the rear surface 36 of interface plate 30, wherein one is associated with filter seat 52, a second is associated with filter seat 58 and the third is associated with filter seat 60.

While not explicitly illustrated herein, it is envisioned and well within the scope of the subject disclosure that an interface plate 30 could be adapted and configured for use only in a smoke evacuation mode, wherein the distal end of the smoke evacuation lumen 88 would be connected to a first valve sealed access device 200 and the distal end of the recirculation supply lumen 90 would be connected to a second valve sealed access device 200. In such an instance, a separate conventional insufflation unit, distinct from the gas supply device 12, could be used for insufflation and pressure sensing.

Figure 23:
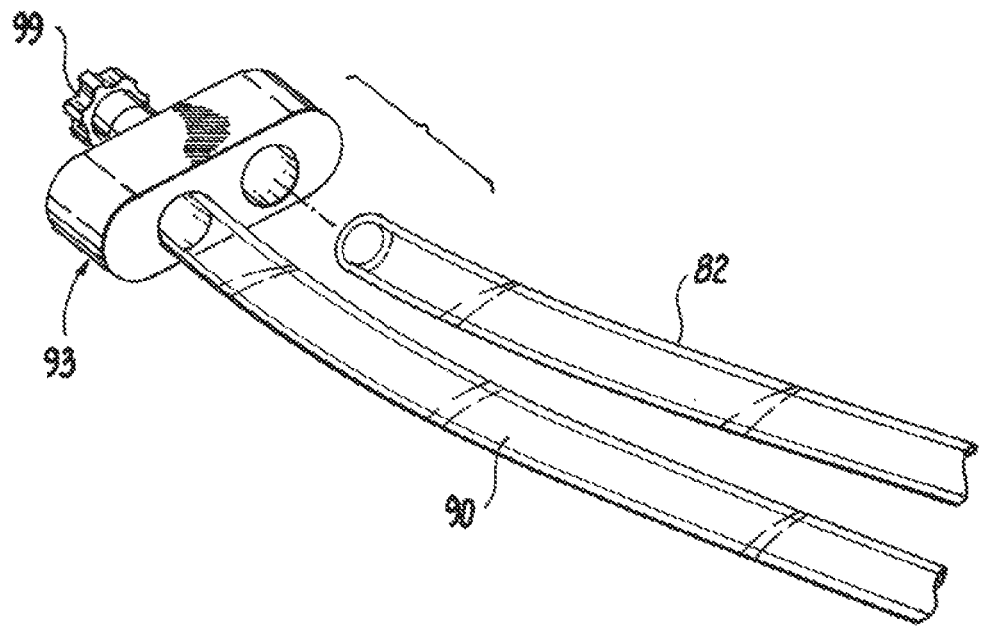
FIGS. 23 and 24 illustrate an alternative arrangement that correspond to FIGS. 11 and 12, wherein the distal end of the insufflation and sensing lumen and a distal end of the recirculation supply lumen are operatively associated with a coupling, which would connect to a first valve sealed access port, and wherein a distal end of the smoke evacuation lumen would be connected to a second valve sealed access port.
Figure 24:
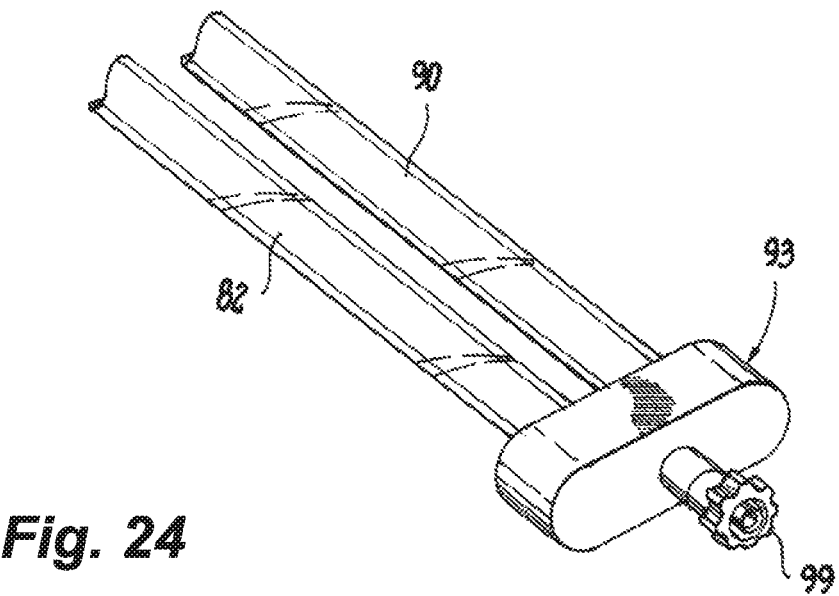

It is also envisioned and well within the scope of the subject disclosure that with respect to the configuration of the interface plate 30 shown in FIGS. 11 and 12, the distal end of the insufflation and sensing lumen 82 and the distal end of the recirculation supply lumen 90 can be operatively associated with a two tube coupling 93, which has a luer type connector 99 for coupling with a first valve sealed access port 200, as illustrated in FIGS. 23 and 24. In this instance, a distal end of the smoke evacuation lumen 88 would be connected to a second valve sealed access port 200.

Figure 13:
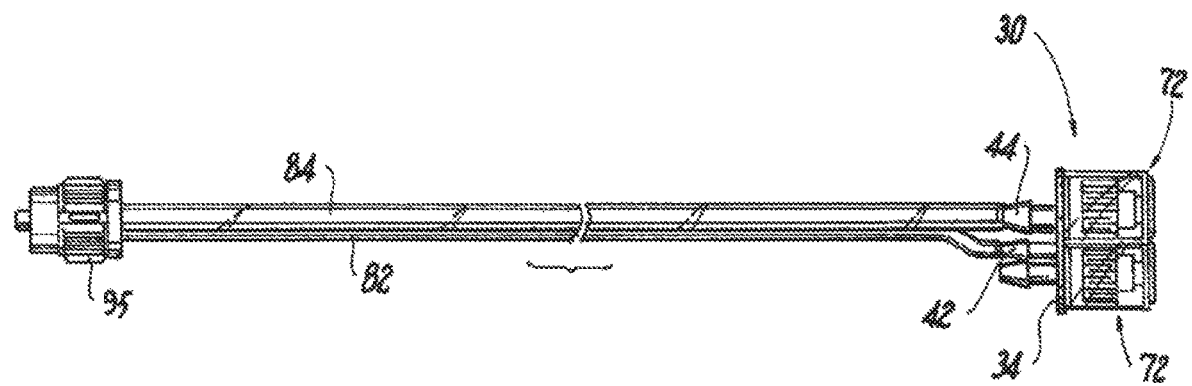
FIG. 13 is a side elevational view and FIG. 14 is a perspective view of the interface plate of the subject invention, wherein an insufflation and sensing lumen, a gas delivery lumen and a gas return lumen are attached thereto, and wherein the distal ends of the three lumens are connected to a tri-lumen coupling, along with three associated filter units.
Figure 14:
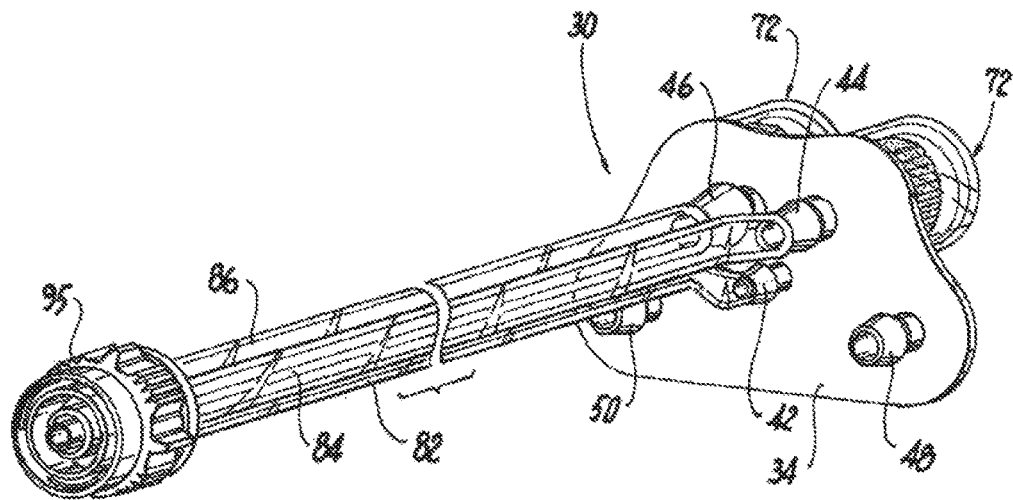

Referring now to FIGS. 13 and 14, there is illustrated another embodiment of the interface plate 30 of the subject invention, which is adapted and configured for use with the gas delivery device 12 in an operating mode that involves insufflation, gas delivery and gas return by way of a dual lumen gas sealed access device 400 of the type disclosed in commonly assigned U.S. Pat. No. 8,795,223, the disclosure of which is herein incorporated by reference. In this instance, the insufflation and sensing lumen 82 is attached to the first connector 42 of the interface plate 30, a gas delivery lumen 84 is attached to the second connector 44 of interface plate 30, and a gas return lumen 86 is attached to the third connector 46 of interface plate 30.

Here, the insufflation and sensing lumen 82, the gas delivery lumen 84 and the gas return lumen 86 are ganged together, and their distal ends are all operatively associated with a tri-lumen coupling 95 of the type which is disclosed in commonly assigned U.S. Pat. No. 9,526,886, the disclosure of which is herein incorporated by reference. The tri-lumen coupling 95 is adapted and configured to connect with the connector 410 of a dual lumen gas sealed access device 400. In this embodiment, there are three filter units 72 associated with the rear surface 36 of interface plate 30, wherein one is associated with filter seat 52, a second is associated with filter seat 54 and the third is associated with filter seat 56.

Figure 15:
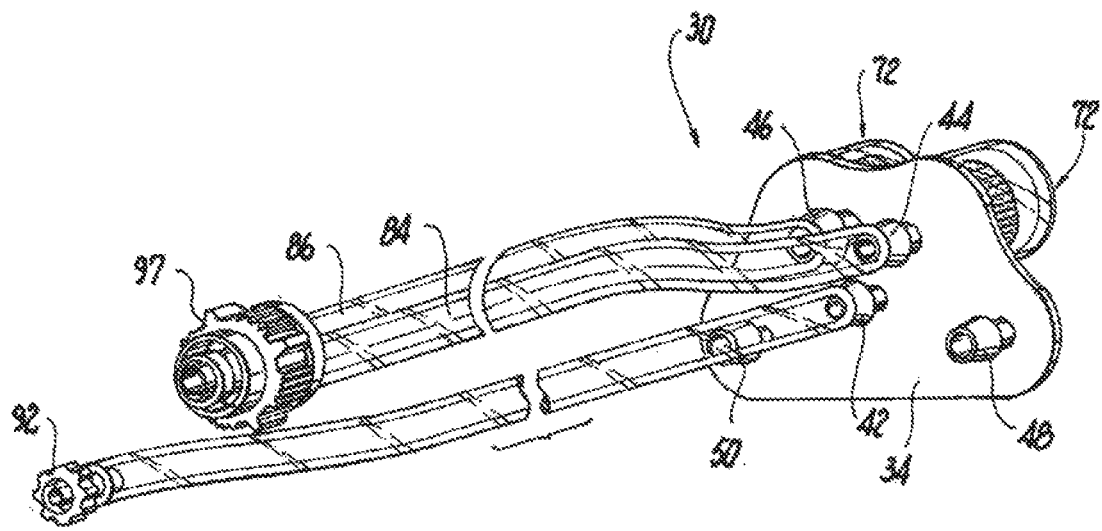
FIGS. 15 and 16 are perspective views of the interface plate of the subject invention, as seen from the front and rear surfaces thereof, wherein an insufflation and sensing lumen is attached thereto, together with a gas delivery lumen and a gas return lumen, and wherein the distal ends of the gas delivery and gas return lumens are connected to a bi-lumen coupling, while the distal end of the insulation lumen is attached to a conventional fitting, along with three associated filter units.
Figure 16:
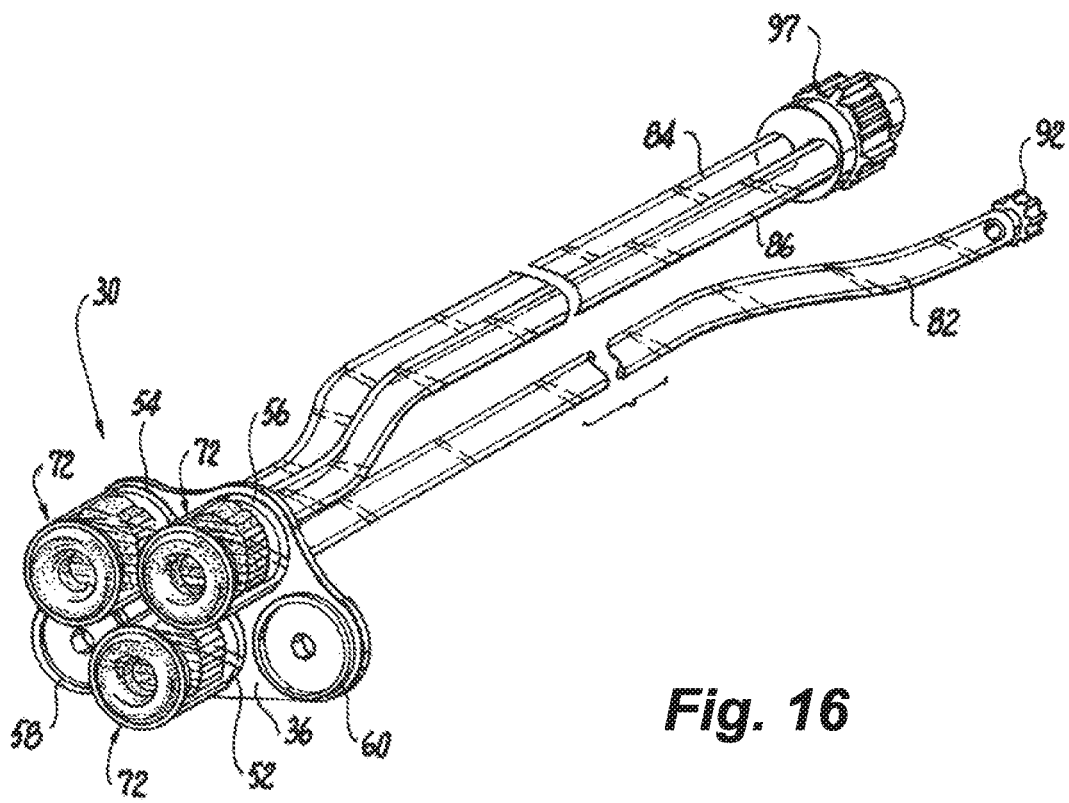

Referring now to FIGS. 15 and 16, there is illustrated yet another embodiment of the interface plate 30 of the subject invention, which is adapted and configured for use with the gas delivery device 12 in an operating mode that involves insufflation by way of a valve sealed access device 200 and pressurized gas delivery and spent gas return by way of a single lumen gas sealed trocar 300, discussed in more detail below with respect to FIG. 1B. In this instance, the insufflation and sensing lumen 82 is attached to the first connector 42 of the interface plate 30, a gas delivery lumen 84 is attached to the second connector 44 of interface plate 30, and a gas return lumen 86 is attached to the third connector 46 of interface plate 30.

Here, the distal end of the insufflation and sensing lumen 82 has a coupling 92 that is adapted and configured to connect with the connector 210 of a valve sealed access device 200, while the gas delivery lumen 84 and the gas return lumen 86 are ganged together, and their distal ends are all operatively associated with a bi-lumen coupling 97 of the type which is disclosed in commonly assigned U.S. Patent Application Publication No. 2017/0361084, the disclosure of which is herein incorporated by reference (see FIGS. 21 through 26).

Figure 1B:
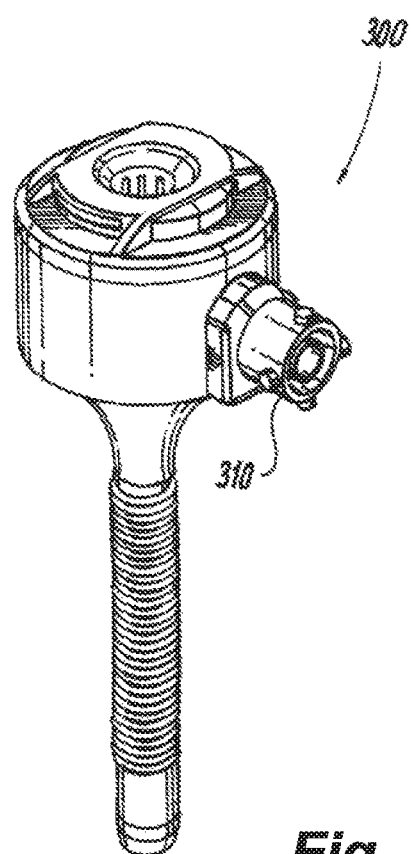
FIG. 1B is a perspective view of a single lumen gas sealed access port with a bi-lumen fitting for coupling with a bi-lumen connector associated with a bi-lumen tube set.
Figure 1C:
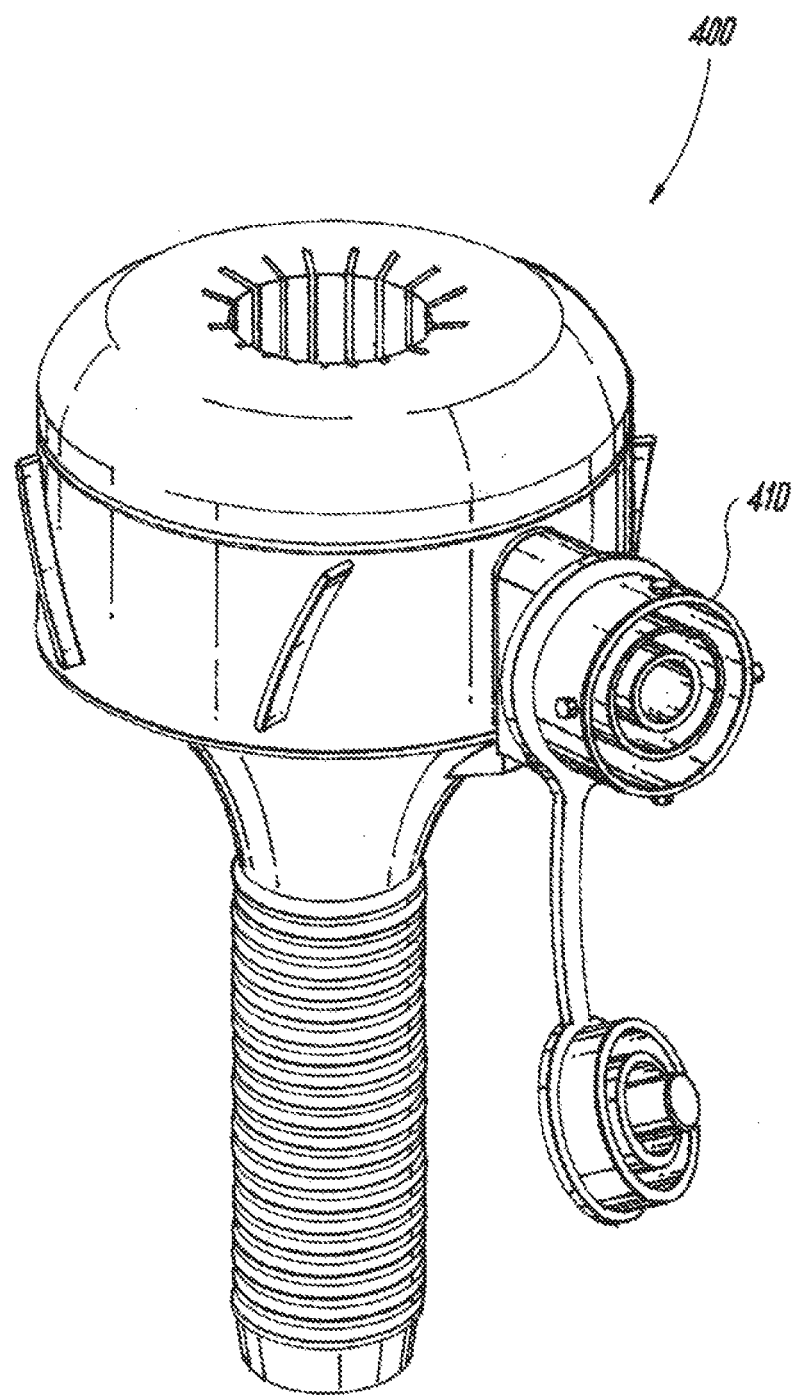
FIG. 1C is a perspective view of a dual lumen gas sealed access port a tri-lumen fitting for coupling with a tri-lumen connector associated with a tri-lumen tube set.

The bi-lumen coupling 97 is adapted and configured to connect with the connector 310 of a single lumen gas sealed access device 300 shown in FIG. 1B, which functions similar to the dual lumen gas sealed access device 400 disclosed in U.S. Pat. No. 8,795,223, except that the bi-lumen gas sealed access device 300 only has a central gas sealed lumen for accommodating instrument passage, it does not have an outer annular lumen surrounding the central lumen, through which insufflation gas is delivered to the surgical cavity of a patient. In all other respects, the device 300 functions like a bi-lumen gas sealed access device 400. In this embodiment, there are also three filter units 72 associated with the rear surface 36 of interface plate 30, wherein one is associated with filter seat 52, a second is associated with filter seat 54 and the third is associated with filter seat 56.

Figure 17:
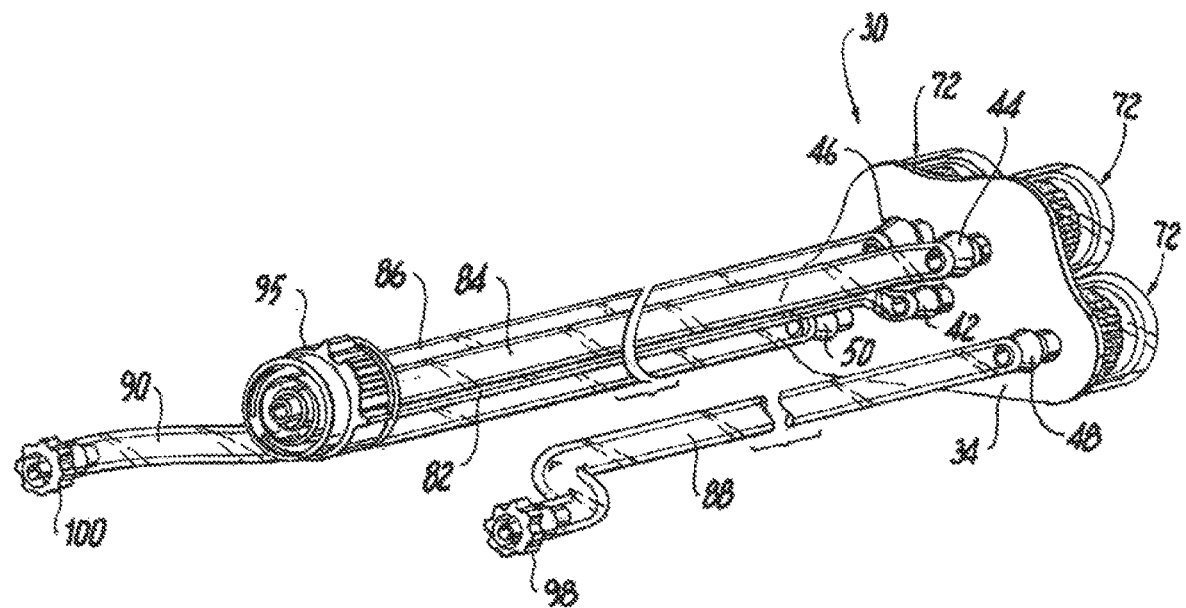
FIGS. 17 through 19 illustrate the interface plate of the subject invention, as viewed from the front side and rear surfaces thereof, wherein an insufflation and sensing lumen, a gas delivery lumen, a gas return lumen, a smoke evacuation lumen and a recirculation supply lumen are all attached thereto, and wherein the distal ends of the insufflation and sensing lumen, gas delivery lumen and gas return lumen are all attached to a tri-lumen coupling, while the distal end of the smoke evacuation lumen and a distal end of the recirculation supply lumen are each attached to a separate conventional fitting, along with five associated filter units.
Figure 18:
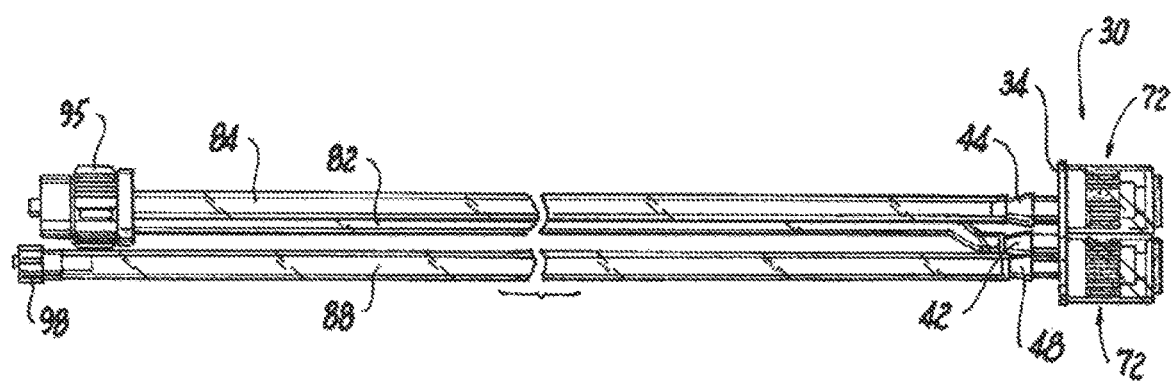
Figure 19:
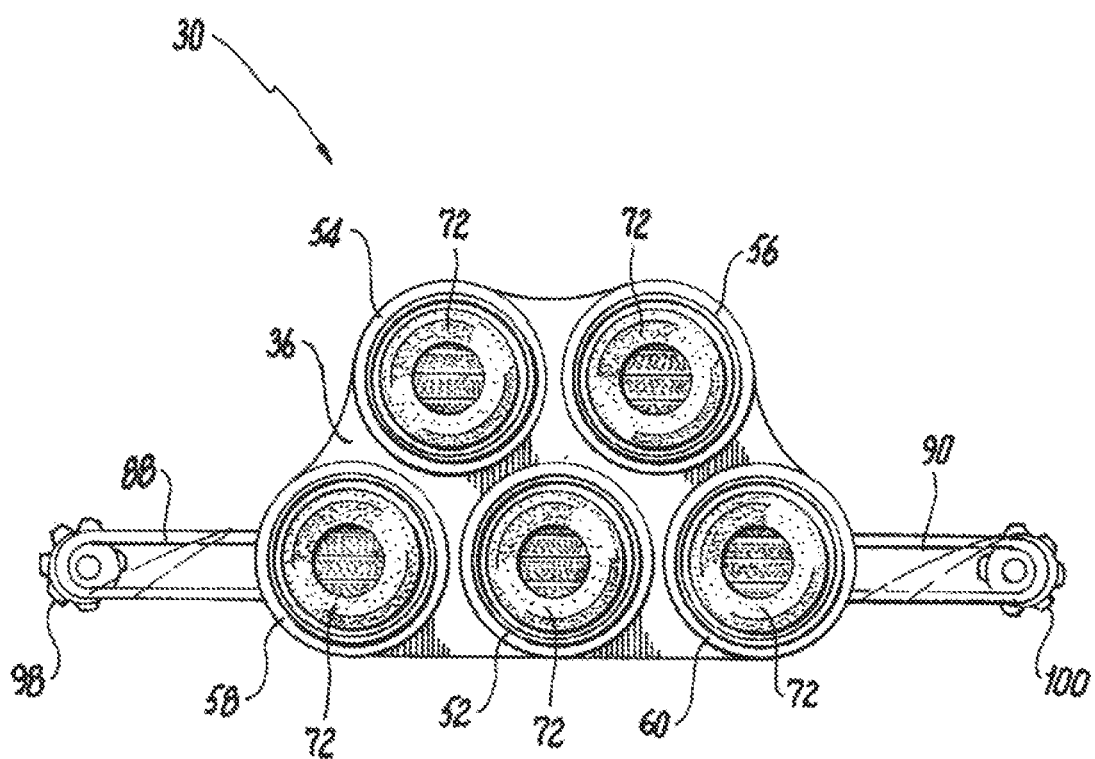

Referring now to FIGS. 17 through 19, there is illustrated an ultimate embodiment of the interface plate 30 of the subject invention, which is adapted and configured for use with the gas delivery device 12 in an operating mode that involves insufflation, pressurized gas delivery and spent gas return by way of a dual lumen gas sealed access device 400. In this instance, the insufflation and sensing lumen 82 is attached to the first connector 42 of the interface plate 30, the gas delivery lumen 84 is attached to the second connector 44 of interface plate 30, the gas return lumen 86 is attached to the third connector 46 of interface plate 30, the smoke evacuation lumen 88 is attached to the fourth connector 48 of the interface plate 30, and the recirculation supply lumen 90 is attached to the fifth connector 50 of the interface plate 30.

Here, the insufflation and sensing lumen 82, the gas delivery lumen 84 and the gas return lumen 86 are ganged together, and their distal ends are all operatively associated with a tri-lumen coupling 95 for connecting with the tri-lumen connector 410 of a bi-lumen gas sealed access device 400, while the smoke evacuation lumen 88 and the recirculation supply lumen 90 have respective couplings 98 and 100 that are each adapted and configured to connect with the connectors 210 of respective valve sealed access devices 200. This embodiment of interface plate 30, with five lumens attached, is the configuration of the subject invention that is illustrated in FIG. 1.

As shown in FIG. 19, in this embodiment of the invention, there are five filter units 72 associated with the rear surface 36 of interface plate 30, wherein one is associated with filter seat 52, a second is associated with filter seat 54, a third is associated with filter seat 56, a fourth is associated with filter seat 58 and a fifth is associated with filter seat 60.

Alternatively, with respect to the 5-lumen configuration of FIGS. 17 through 19, while not illustrated explicitly, it is envisioned and well within the scope of the subject disclosure, that the distal ends of the gas delivery lumen 84 and the gas return lumen 86 could be attached to a bi-lumen coupling 97, that is adapted and configured to connect with a single lumen gas sealed access device 300, a distal end of the insufflation and sensing lumen 82 could be connected to a first valve sealed access device 200, a distal end of the smoke evacuation lumen 88 could connected to a second valve sealed access device 200 and a distal end of the recirculation supply lumen 90 could be connected to a third valve sealed access device 200.

It is also envisioned and well within the scope of the subject disclosure that the interface plate 30 of the subject invention would include a mechanism for communicating information to the controller 16 in the gas delivery device 12 identifying which of the five lumens and filters is attached to the interface plate 30, and thereby indicate which particular operational mode must be activated to perform a desired surgical procedure. This mechanism could be a mechanical feature, such as a micro-switch that would communicate with the controller 16 when the interface plate 30 is installed within the reception cavity 32 in the front face of gas delivery device 12. Alternatively, the mechanism could be wireless transmitter 35 on the rear surface 36 of interface plate 30, as shown in FIG. 4, such as an RFID signal transmitter or NFC signal transmitter, that would communicate information to the controller 16 of gas delivery device 12 related to the types of lumens associated with the interface plate 30.

Figure 20:
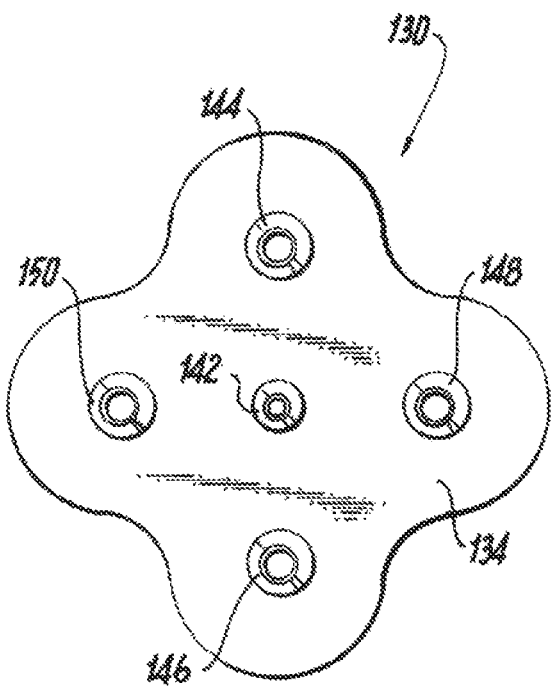
FIGS. 20 through 22 are illustrations of another embodiment of an interface plate constructed in accordance with a preferred embodiment of the subject invention, which has permanent filter canister corresponding to the insufflation path, wherein a single sheet of filter media is installed.
Figure 21:
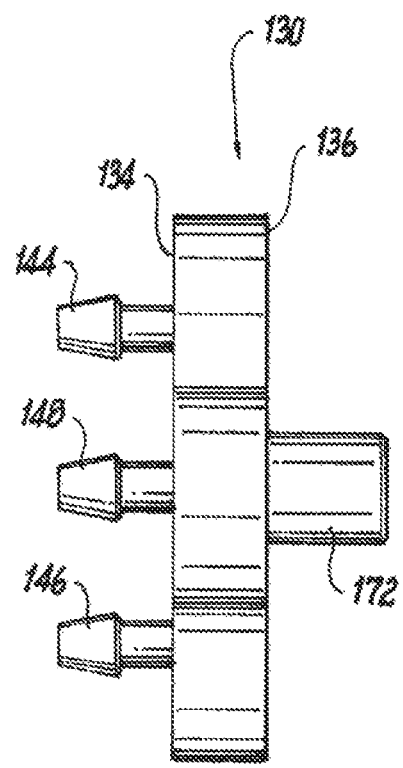

Referring to FIGS. 20 through 23, there is illustrated another embodiment of an interface plate constructed in accordance with a preferred embodiment of the subject invention, which is designated generally by reference numeral 130. The front surface 134 of interface plate 130 includes a first connector 142 for connecting with an insufflation and sensing lumen, a second connector 144 for connecting with a gas delivery lumen, a third connector 146 for connecting with a gas return lumen, a fourth connector 148 for connecting with a smoke evacuation lumen and a fifth connector 150 for connection with a recirculation supply lumen, as best seen in FIGS. 20 and 21.

Figure 22:
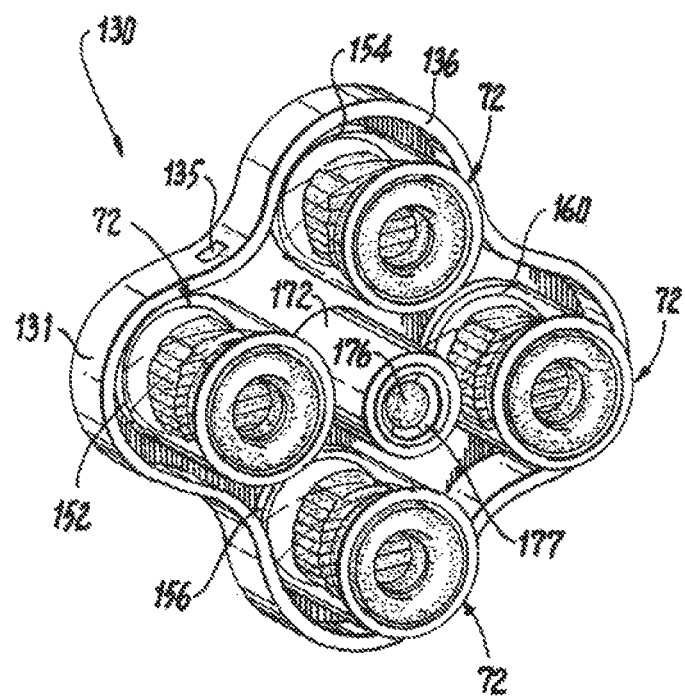

Referring to FIG. 22, the rear surface 136 of interface plate 130 includes a circular filter seat 154 for communicating with the connector 144, a circular filter seat 156 for communicating with connector 146, a circular filter seat 158 for communicating with connector 148, and a circular filter seat 160 for communicating with the 150. Each filter seat is adapted and configured for accommodating a filter module 72 of the type illustrated in FIGS. 5 and 6.

As best seen in FIGS. 21 and 22, the interface plate 130 has an integral filter canister 172 that corresponds to the insufflation path associated with connector 142. This integral filter canister includes a single sheet of filter media 176 supported in an annular disc 177, for filtering insufflation gas delivered to the surgical cavity of a patient. It should be appreciated that the insufflation path associated with connector 142 is employed in nearly every embodiment or version of the interface plates described herein, therefore it would be advantageous to provide the filter canister 172 as an integral feature of the interface plate 130, while each of the others paths of interface plate 130 would communicate with a filter module 72.

A shroud 136 surrounds the entire periphery of the interface plate 130 and forms a mounting surface for a wireless transmitter 135, such as an RFID signal transmitter or NFC signal transmitter, identifying which of the five lumens is attached to the interface plate 130.

While the subject disclosure has been shown and described with reference to preferred embodiments, those skilled in the art will readily appreciate that changes or modifications may be made thereto without departing from the scope of the subject disclosure.

What is claimed is:

1. A multi-modal gas delivery device for performing an endoscopic surgical procedure in a surgical cavity, comprising:
    a) an insufflation subunit for delivering insufflation gas from a gas source to the surgical cavity and for sensing pressure within the surgical cavity by way of a first connector on an interface plate configured to engage with the gas delivery device;
    b) a primary gas circulation pump for delivering pressurized gas to a gas sealed access port by way of a second connector on the interface plate so as to generate a gaseous seal therein and thereby maintain a stable pressure within the surgical cavity and for receiving gas returning from the gas sealed access port that was used to form the gaseous seal by way of a third connector on the interface plate; and
    c) a secondary gas circulation pump for continuously evacuating smoke filled gas from the surgical cavity by way of a fourth connector on the interface plate, regardless of the sensed pressure within the surgical cavity.

2. The multi-modal gas delivery device as recited in claim 1, wherein the secondary gas circulation pump is further configured to return filtered gas to the surgical cavity by way of a fifth connector on the interface plate.

3. The multi-modal gas delivery device as recited in claim 2, further comprising a controller for initiating an operating mode from a group of operating modes including:
    i) an insufflation mode driven by the insufflation subunit;
    ii) an insufflation and gas circulation mode driven by the insufflation subunit and the primary gas circulation pump;
    iii) a smoke evacuation and gas return mode driven by the secondary gas circulation pump;
    iv) an insufflation and smoke evacuation mode driven by the insufflation subunit and the secondary gas circulation pump;
    v) an insufflation, smoke evacuation and gas return mode driven by the insufflation subunit and the secondary gas circulation pump; and
    vi) an insufflation and gas circulation mode driven by the insufflation subunit and the primary gas circulation pump, together with smoke evacuation and gas return driven by the secondary gas circulation pump.

4. The multi-modal gas delivery device as recited in claim 3, wherein the controller is adapted and configured to determine which operating mode to initiate based upon information received from the interface plate.

5. The a multi-modal gas delivery device as recited in claim 4, wherein the information received from the interface plate is communicated to the gas delivery device by way of an rfid communication link, an nfc communication link, a bluetooth communication link, a wifi communication link or by way of microswitches.

\* \* \* \* \*